(12) United States Patent
Wintersperger et al.

(10) Patent No.: US 7,150,874 B2
(45) Date of Patent: *Dec. 19, 2006

(54) VECTOR FOR INTEGRATION OF HETEROLOGOUS SEQUENCES INTO POXVIRAL GENOMES

(75) Inventors: Stefan Wintersperger, Icking (DE); Robert Baier, Oberschleissheim (DE); Gerd Sutter, München (DE); Marion Ohlmann, München (DE); Volker Erfle, München (DE)

(73) Assignee: GFS Forschungszentrum fur Umwelt und Gesundheit GmbH, Neuherberg (DE)

( * ) Notice: Subject to any disclaimer, the term of this patent is extended or adjusted under 35 U.S.C. 154(b) by 287 days.

This patent is subject to a terminal disclaimer.

(21) Appl. No.: 10/668,521

(22) Filed: Sep. 23, 2003

(65) Prior Publication Data

US 2004/0228840 A1 Nov. 18, 2004

Related U.S. Application Data

(63) Continuation of application No. 09/980,029, filed as application No. PCT/EP00/04786 on May 25, 2000, now Pat. No. 6,682,742.

(30) Foreign Application Priority Data

May 28, 1999 (DK) ............... 1999 00753

(51) Int. Cl.
- *A61K 39/285* (2006.01)
- *A61K 39/275* (2006.01)
- *C12N 7/01* (2006.01)
- *C12N 15/39* (2006.01)
- *C12N 15/863* (2006.01)

(52) U.S. Cl. ............... 424/199.1; 435/235.1; 435/320.1; 435/471; 435/91.41; 435/325; 435/490; 536/23.72

(58) Field of Classification Search ............ 435/320.1, 435/235.1, 471, 91.41, 325, 472, 474, 477, 435/490; 536/23.72; 424/199.1
See application file for complete search history.

(56) References Cited

U.S. PATENT DOCUMENTS

| | | | | |
|---|---|---|---|---|
| 5,185,146 A | * | 2/1993 | Altenburger | 424/199.1 |
| 5,364,773 A | * | 11/1994 | Paoletti et al. | 435/69.1 |
| 6,440,422 B1 | * | 8/2002 | Sutter et al. | 424/199.1 |
| 6,682,742 B1 | * | 1/2004 | Wintersperger et al. | 424/199.1 |

FOREIGN PATENT DOCUMENTS

| | | | |
|---|---|---|---|
| EP | 261925 | * | 3/1988 |
| WO | WO 96/39491 | * | 12/1996 |
| WO | WO97/02355 | * | 1/1997 |
| WO | WO 00/73476 | * | 12/2000 |

OTHER PUBLICATIONS

Antoine et al (Virology 244:365-396, 1998).*
Meyer et al, Mapping of deletions in the genome of the highly attenuated vaccinia virus MVA and their influence on virulence, "Journal of General Virology", 1991 pp. 1031-1038.

* cited by examiner

*Primary Examiner*—Mary E. Mosher
(74) *Attorney, Agent, or Firm*—Jonathan Myers; Andrew Wilford

(57) ABSTRACT

A new DNA vector is disclosed comprising a nucleic acid sequence useful for inserting heterologous sequences into the genome of poxviruses by homologous recombination. Also disclosed are recombinant poxviruses carrying heterologous coding sequences transferred by the DNA vector.

36 Claims, 2 Drawing Sheets

VECTOR FOR INTEGRATION OF HETEROLOGOUS SEQUENCES INTO POXVIRAL GENOMES

CROSS REFERENCE TO RELATED APPLICATIONS

This application is a continuation of application Ser. No. 09/980,029 filed 26 Dec. 2001, now U.S. Pat. No. 6,682,742, which is the US National Phase of PCT/EP00/04786 filed 25 May 2000 and which claims the benefit of the priority of Danish Patent Application PA 19 99 00753 filed 28 May 1999.

FIELD OF THE INVENTION

The present invention provides a new DNA vector comprising a nucleic acid sequence useful for inserting heterologous sequences into the genome of poxviruses by homologous recombination. The present invention relates also, inter alia, to recombinant poxviruses carrying heterologous coding sequences transferred by the vector according to the present invention.

BACKGROUND OF THE INVENTION

The successful worldwide eradication of smallpox via vaccination with live Orthopoxvirus, such as Vaccinia virus strain Western Reserve, Copenhagen or Ankara, stimulated in the early 80's research to study poxvirus s in closer detail. Subsequently, said poxviruses were developed to well understood and easy-to-handle virus vectors or research tools, respectively (Moss, 1996). Today poxvirus vectors are used in various fields e.g. as expression vector or for the development of vaccines and therapeutic substances. The main reasons for the high acceptance of poxvirus vectors are the following promising features: Firstly, the vector viruses are easy to manipulate, are highly stable and cheap to manufacture. Secondly, said vector virus can accommodate large amounts of heterologous DNA and has proved to be a versatile expression vector. Thirdly, said vector virus is easily administered in vivo and has succeeded in stimulating humoral and cellular immune responses. Accordingly, its use as a recombinant vaccine for protective immunization against infectious disease or cancer made poxvirus vectors particularly attractive. Especially, Vaccinia virus, the best-known member of the Orthopoxvirus family, has been successfully used as recombinant vaccine to protect against diseases in a large variety of animal models (Carroll et al., 1997; Sutter et al., 1994a).

To develop and establish recombinant vaccinia viruses several insertion sites have been used. The most prominent insertion site of the vaccinia genome is the locus of the viral thymidine-kinase (tk) gene (Mackett et al., 1982). However, also other non-essential genes, such as the viral hemagglutinin and ribonucleotide reductase genes (Shida et al. 1987, Howley et al. 1996) or the naturally occurring deletion site II or III have been used to insert heterologous DNA sequences into the genome of vaccinia virus (Sutter et al., 1994a). Construction of recombinant vector viruses carrying several heterologous genes or several immunogenic epitopes becomes more and more of general interest. Accordingly, there is a high need to identify further sites in the virus genome, which are suitable for insertion of further heterologous DNA sequences.

Insertion of heterologous DNA sequences into a poxviral genome bears the risk to destroy regions essential for the virus propagation due to a lack of complete understanding of the poxviral life cycle. Although the sequence information of several poxvirus genomes (Goebel et al. 1990; Antoine et al. 1998) is available, the function of most proteins encoded by the identified open reading frames is not known. Accordingly, it is still a complicated challenge to identify sites in the genome, which are suitable to stably take up heterologous DNA without destroying any sequences essential for viral replication and propagation.

OBJECT OF THE INVENTION

It is thus an object of the present invention to identify a new insertion site in the poxviruses genome and provide vectors suitable to direct the integration of heterologous DNA sequences into said insertion site.

DESCRIPTION OF THE INVENTION

To achieve the foregoing and other objects, the present invention provides a vector comprising a nucleic acid sequence according to SeqID No. 1 or its complementary strand. The nucleic acid sequence according to SeqID No. 1 is highly homologous with parts of the genomic sequences of a poxvirus genome. Due to this homology the nucleic acid sequence according to the present invention is capable to initiate homologous recombination between said sequence and the corresponding genomic sequences of poxviruses. Thus, the present invention provides a means useful to direct integration of DNA sequences into the genome of different orthopoxviruses, preferably into the genome of modified vaccinia virus Ankara (MVA), but also of further related orthopoxviruses such as, e.g., Vaccinia virus strain Western Reserve or Copenhagen.

According to a preferred embodiment the nucleic acid sequence of the present invention is derived from modified vaccinia Ankara virus (MVA), especially from MVA, which has been isolated and deposited on Jan. 27th, 1994 according to the Budapest Treaty at the European Collection of Animal Cell Cultures (Salisbury, UK) under Deposit No.: V94012707.

The present invention further provides a vector comprising nucleic acid sequences, which hybridize under stringent conditions to the sequences according to SeqIDNo:1 or its complementary strand. In the context of this invention the term "vector" is understood as DNA vehicles of circular structure, such as plasmids, cosmids or artificial chromosomes. Said vector comprises in addition to the desired nucleic acid sequence regulatory seq fences, selective marker genes and replicons enabling the autonomous replication of the vector. Hence, the vector according to the present invention can easily be amplified in and isolated from unicellular host organism. Furthermore, the term "under stringent conditions" defines parameters according to standard protocols (Sambrook et al., 1989), such as reaction temperature, formamide content or salt concentrations, which allow hybridization of DNA-DNA sequences with a homology about and above 70%. As described above, these sequences also hybridize to the corresponding sequence of the poxvirus genome and are thus, particularly, useful to integrate heterologous sequences into a genome of orthopoxviruses.

Additionally, the present invention provides a vector comprising fragments of the above-mentioned nucleic acid sequence. These fragments comprise consecutive base pairs of said nucleic acid sequence and are also useful to integrate into the poxviral genome by homologous recombination.

The length of said fragments is variable and fragments with only 30 base pairs being homologous to corresponding parts of the poxvirus genome are already sufficient to initiate recombination events. However, to increase the efficiency of homologous recombination between the poxvirus genome and the fragments as used in the present invention, said fragments are preferably about and above 200 base pairs in length, more preferably about and above 300 or 500 base pairs in length.

To initiate homologous recombination the vector according to the present invention and a wild type poxvirus are introduced into a host cell. During replication of the poxvirus genome homologous recombination between the nucleic acid sequence inserted into the vector and the corresponding sequences of the poxvirus genome occurs. Since homologous recombination events occur only with a statistical probability of 1:10 3 to 1:10 4 any resulting recombinant poxvirus needs to be isolated. For this, e.g. a marker gene with functionally associated regulatory element is inserted into a cloning site of the nucleic acid sequence included in the vector. After homologous recombination the resulting recombinant poxviruses are isolated by screening for expression of said marker gene or by selection for the expression of a dominant-selection marker gene, respectively.

According to a further embodiment the vector of the present invention is particularly useful for insertion of a desired heterologous coding sequence into a poxviral genome. The term “heterologous” is used in the context of this invention for any combination of nucleic acid sequences that is not normally found intimately associated in nature. The heterologous genes according to the present invention are preferably selected from the group of marker genes, therapeutic genes, such as anti-viral genes, anti-tumor genes, cytokine or chemokine genes, suicide genes, but also from host range genes or immunogenic epitopes. For insertion and/or expression of a desired heterologous coding sequences into a poxviral genome said heterologous coding sequence is inserted at a cloning site within the nucleic acid sequence.

In general, a cloning site is a restriction enzyme recognition site. According to the present invention the preferred cloning site for the insertion of heterologous sequences is the restriction enzyme recognition site of the EcoRI enzyme. This EcoRl site is unique in the nucleic acid sequence of the present invention, and is located between the two ORFs included in said nucleic acid sequence (FIG. 1). Beside this, any further restriction enzyme recognition site, which is located in the non-coding regions between said two ORFs can be used as cloning site. Surprisingly, also any cloning site located in one of the ORFs can be used for the insertion of heterologous sequences. Particularly, the inventors found that the destruction of said ORFs by such insertion into the ORFs does not hamper the viral life cycle or replication efficiency, respectively. Additionally, it was found by the inventors that the use of fragments according to the invention, which are incorporated in the vector to initiate homologous recombination, likewise did not interfere with viral propagation or replication efficiency.

Generally, heterologous sequences to be integrated into a viral genome by homologous recombination are flanked on both ends by sequences being homologous to corresponding sequences of the viral genome. However, the present invention also includes vectors wherein the heterologous sequence is only flanked on one side by the above-mentioned nucleic acid sequence. According to the present invention also vectors comprising only one fragment and a desired heterologous sequence are useful to insert said heterologous sequence into a poxvirus genome.

To guarantee expression of an inserted heterologous coding sequence at least one transcriptional control element is additionally inserted into the cloning sites. This transcriptional control element is in functional association with the heterologous coding sequence, thereby controlling and/or allowing its expression. According to a further preferred embodiment of the present invention the transcription control element is derived from a poxvirus and/or is a consensus sequence of a poxvirus derived transcription control element.

According to still a further embodiment of the present invention the vector comprises at least two recombinogenic sequences, which flank one or more heterologous coding sequences, particularly sequences encoding e.g. a marker or a host range gene, and/or the transcription control element(s) inserted into the cloning site. The term “recombinogenic sequences” describes nucleic acid sequences, which, due to their similar or nearly identical structure, are capable to delete any sequence between said recombinogenic sequences by intragenomic homologous recombination. Accordingly, the sequences flanked by said recombinogenic nucleic acid sequences are only transiently inserted into the viral genome and are, subsequently, completely deleted. This deletion of sequences flanked by recombinogenic sequences is of particular interest for the isolation of recombinant poxviruses, which should comprise only a heterologous coding sequence encoding a therapeutic or immunogenic gene, but no further marker or host range gene. For this, the marker gene, the host range gene and/or eventually also the transcription control element(s), but not the desired heterologous coding sequence, e.g. a therapeutic gene or immunogenic epitopes, are flanked by such recombinogenic sequences. After isolation of the recombinant virus, which is performed under a selection pressure upon the marker gene or the host range gene, the selection pressure is removed and thus, intragenomic homologous recombination to delete the marker or host range gene is allowed.

The present invention, furthermore, provides a recombinant poxvirus comprising in its genome the nucleic acid sequence transferred by the vector according to the present invention. Most preferably, this recombinant poxvirus is a recombinant MVA virus.

A further embodiment of the invention provides a method of treatment and/or prevention of an infectious disease or proliferative disorder. Said method comprises infection—either in vivo or in vitro—of a target cell population with recombinant poxviruses according to the present invention. Alternatively, according to this method the target cells are transduced—either in vivo or in vitro—with the vector according to the present invention and are infected, simultaneously or with a timelag, with any orthopoxvirus, including the recombinant poxvirus of the present invention. In this case, the poxvirus provides the cell with the poxviral replication and transcription machinery. As a consequence, the desired heterologous coding sequence incorporated in the vector and controlled by a poxvirus-derived transcriptional control element is expressed in the target cell. Target cells, which have been transduced or infected in vitro, can then according to the method of the present invention be applied to a living animal body, including a human.

The invention provides the vector, the recombinant poxvirus and/or the target cells of the present invention useful for the treatment and/or prevention of an infectious disease or proliferative disorder. Furthermore, the vector, the recombinant poxvirus and/or the target cells according to the present invention are used for the production of a pharmaceutical composition, especially a vaccine, which is useful for in vivo and in vitro gene delivery and/or vaccination of mammals including humans, as described above.

SUMMARY OF THE INVENTION

The present invention, inter alia, comprises the following alone or in combination:

A vector for insertion of heterologous coding sequences into a poxviral genome, said vector including a nucleic acid sequence comprising one or more elements selected from the group consisting of:

(a) the nucleic acid sequence according to SeqID No. 1 or its complementary strand;

(b) a nucleic acid sequence which hybridizes under stringent conditions to the sequences as defined in (a);

(c) a fragment comprising at least 30 consecutive base pairs of the nucleic acid sequences as defined in (a) or (b);

the vector as above wherein the nucleic acid sequence is derived from a modified vaccinia Ankara virus (MVA);

the vector as above wherein additionally at least one transcriptional control element is included into at least one cloning site of said nucleic acid sequence;

the vector as above wherein the transcriptional control element is derived from a poxvirus genome or is the consensus sequence of a poxvirus derived transcriptional control element;

the vector as above additionally comprising at least one heterologous coding sequence, said heterologous coding sequence functionally associated with the transcriptional control element as above;

the vector as above wherein the heterologous coding sequence is selected from the group of marker genes, therapeutic genes, host range genes and/or immunogenic epitopes;

the vector as above comprising a recombinogenic sequence, which flanks one or more heterologous coding sequences encoding marker genes, host range genes and/or the transcriptional control element as above;

a recombinant poxvirus comprising in its genome the nucleic acid sequence transferred by the vector as above;

the recombinant poxvirus as above wherein the poxvirus is a modified vaccinia Ankara virus (MVA);

a method of introducing a heterologous sequence into poxvirus genome comprising (a) transduction of a host cell with the vector as above (b) infection of said host cell with a poxvirus, and (c) isolation of recombinant poxviruses;

a method of treatment and/or prevention of an infectious disease or proliferative disorder of a living animal body, including a human, comprising application to said living animal body the recombinant poxvirus as above, and/or the vector as above, or application of said vector with any other poxvirus;

the method as above wherein the recombinant poxvirus is derived from an orthopoxvirus;

a target cell comprising the recombinant poxvirus as above and/or the vector as above;

the vector as above, the recombinant poxvirus as above and/or the target cell as above for the treatment and/or prevention of an infectious disease or proliferative disorder;

the use of the vector as above, the recombinant poxvirus as above and/or the tar get cell as above for the production of a medicament for the treatment and/or prevention of an infectious disease or proliferative disorder;

a pharmaceutical composition comprising the vector as above, the recombinant poxvirus as above and/or the target cell as above, and a pharmaceutical acceptable carrier and/or diluent;

a pharmaceutical composition comprising the vector as above, a poxvirus, except the recombinant poxvirus as above, and a pharmaceutical acceptable carrier and/or diluent.

The following example will further illustrate the present invention. It will be well understood by a person skilled in the art that the provided example in no way may be interpreted in a way that limits the applicability of the technology provided by the present invention to this example, and the invention is therefore to be limited only by the full scope of the appended claims.

EXAMPLE 1

Construction of the Insertion Vector

To obtain sequences suitable for recombination into a poxviral genome, a DNA fragment derived from the modified vaccinia Ankara virus (deposited according to the Budapest Treaty under Deposit No.: V94012707 at the European Collection of Animal Cell Cultures in Salisbury, UK) was amplified by conventional PCR using the following oligonucleotide primers:

```
A24R_1;5'- CCGAAGCTTAATGAACGCCAGAGG- 3',   SeqID
                                          No.: 2;

A27L_1c;5'- AGGCTCGAGTAAGAGCGGCTATGAT- 3',  SeqID
                                          No.: 3.
```

Figure 1:
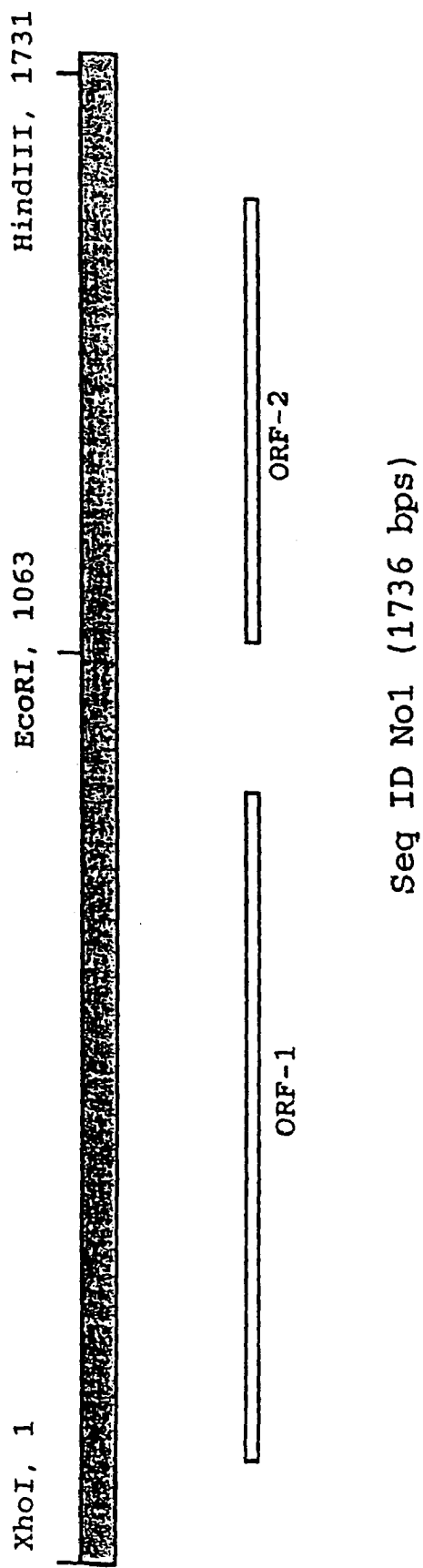
FIG. 1 is a map of the polynucleotide having Seq. ID No:1 with restriction sites xhoI.1, EcoRI, and Hind III and open reading frames ORF-1 and ORF-2.
Figure 2:
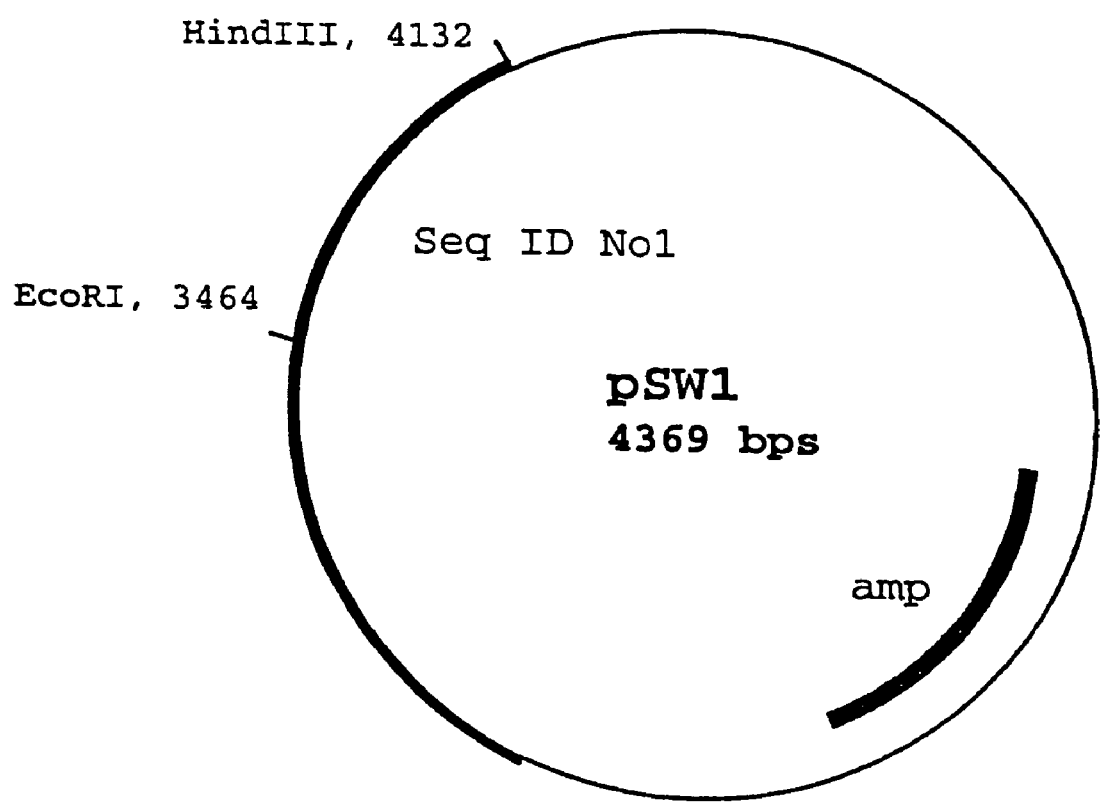
FIG. 2 is a map of plasmid pSW1 comprising the polynucleotide having Seq. ID No: 1.

The oligonucleotide primers comprise, close to the 5' end and marked by underlining, a recognition sequence for the restriction enzymes HindIII (SeqID No.: 2) or XhoI (SeqID No.: 3) for subcloning of the resulting amplification product into a cloning vector. Accordingly, the specifically amplified sequence (SeqID No.: 1), which has a molecular weight of 1.7 kb, was subcloned SalI/HindIII into a pUC19 cloning plasmid (GenBank Accession No.: X02514). The resulting plasmid was designated pSW1 (FIG. 2).

The subcloned insert has been sequenced, and this sequence was compared to other known sequences from vaccinia virus strains Copenhagen, WR, and MVA. It was found that said sequence comprises parts of the sequence of the MVA-ATI region. The ATI gene of most orthopoxviruses form a dense cytoplasmic matrix embedding mature virions, so called inclusion bodies, which can be visualized by light microscopic examination of infected cells. Proposed ATI function is to provide higher stability and prolonged dissemination of infectious virus particles in the general environment. Among the orthopoxviruses are several members including ectromelia virus, cowpox virus and racoon poxvirus produce this typical inclusion protein with a size of 130 to 160 kDa. However, other members of the orthopox genus, as e.g. vaccinia virus Western Reserve (WR), vaccinia virus Copenhagen or MVA, form no such inclusion bodies. This is a result of sequence deletions or frame-shift mutations leading to loss of coding sequence and resulting in a truncated ATI-homologue. For example vaccinia virus WR expresses a 94 kDa ATI-homologue, while MVA and vaccinia virus strain Copenhagen expresses no such ATI-homologue.

For the further construction of insertion vectors, a naturally occurring recognition site of the restriction enzyme EcoRI was used to split the amplified sequence into two segments. These segments serve as flanking regions (flank1, flank2), that initiate homologous recombination with a poxvirus genome. In between these flanking regions, vaccinia virus promoter sequences—e.g. of the 7,5 promoter (7.5) and/or the synthetic promoter (sP)—as well as multiple cloning sites for the insertion of operably heterologous genes have been inserted. The resulting plasmids are designated pSW-7.5-sP, pSW-7.5, pSW-sP.

Additionally an expression cassette comprising the vaccinia virus host rage gene, K1L, fused to the EGFP fusion gene (isolated from the plasmid pEGFP, Clonetech, GenBank Accession #: U76561) and the naturally occurring K1L promoter, was inserted between the flanking regions as described above. This expression cassette is especially helpful for efficient sel action and isolation of recombinant viruses. The resulting plasmid is designated pSWkllgfp.

Generation of Recombinant Virus

For the generation of recombinant viruses 6-well tissue culture plates with cell monolayers of about 80% confluence are used. For the generation of recombinant MVA permissive cells such as chicken embryo fibroblasts are used. For the generation of recombinant vaccinia viruses of the strain WR African Green Monkey (Vero) cells have been used.

Firstly, the cell culture medium is discarded and the cells overlaid with serum-free medium containing wild-type poxvirus at a multiplicity of infection (MOI) of 0.01 (e.g. an inoculum 5×1031U (infectious units) in 1 ml medium for one well with 5×105 cells). This mixture is incubated for 1 hour at 37° C. in 5% C02-atmosphere. Then, the inoculum is removed and the cells are washed twice with 2 ml OptiMEM per well. Subsequently, the cell monolayer is overlaid with Lipofectin/plasmid DNA-mix (total volume: 1 ml) prepared as described by the manufacturer (GIBCO BRL) and using 15=lg plasmid DNA, of the pSWkllgfp. The mixture I s incubated for 5–12 hours at 37° C. in 5% C02-atmosphere. Then, the Lipofectin/plasmid DNA-mix is removed and the cells overlaid with 1.5 ml fresh medium supplemented with 10% FCS. At 48 hours after infection, cell monolayer is detached with a cell scraper and the cells and medium are transferred into 2 ml-microcentrifuge tubes. The transfection harvest is stored at −20 to −80° C. Upon transfection of the plasrnid pSWkllgfp into poxvirus infected cells, the host range gene KIL fused to the EGFP gene were precisely recombined into the site of the poxvirus genome, which is homologous with the flanking regions in the vector plasmid.

To isolate recombinant MVA viruses from non-recombinant MVA viruses a host range cell, rabbit kidney (RK)13, was infected with virus material obtained from the transfection experiment as described above. Previous work had shown that MVA infection of rabbit RK13 cells results in an early block of viral replication characterized by impaired synthesis of intermediate viral RNA and lacking replication viral DNA. However, this non-productive NVA infection of RK13 cells could be overcome by coexpression of the vaccinia virus host range gene K1L (Sutter et al., 1994b). Accordingly, inoculation of virus material obtained from said transfection experiments into RK13 cultures resulted in the highly selective growth only of recombinant viruses, which coexpressed the KM gene. After five consecutive passages on RK13 cells grown in 6-well or 96-well tissue culture plates the virus MVA-KILGFP was isolated. The absence of nonrecombinant MVA was demonstrated by PCR.

Additionally, the expression of the fused EGFP gene allowed a direct monitoring of infection with recombinant virus via GFP fluorescence. The direct monitoring is also used to identify and then isolate recombinant Vaccinia viruses of the strain WR, which are not sensitive to a K1L selection.

REFERENCES

Antoine, G. et al., 1998, The complete genomic sequence of the modified vaccinia Ankara strain: comparison with other orthopoxviruses. Virology, 5 May 10; 244(2):365–96.

Carroll, M. W. et al. 1997: Highly attenuated modified vaccinia virus Ankara (MVA) as an effective recombinant vector: A murine tumor model. Vaccine 15, 387.

Fenner, F. et al. 1988: Smallpox and its eradication. World Health Organisation, Geneva.

Goebel, S J. et al., 1990, The complete DNA sequence of vaccinia virus. 15 Virology, November;179(l):247–66, 517–63.

Howley, P M. et al., 1996, A vaccinia virus transfer vector using a GUS reporter gene inserted into the 14L locus. Gene, June 26;172(2):233–7.

Mackett, M. et al. 1982: Vaccinia virus: a selectable eukaryotic cloning and expression vector. Proc. Natl. Acad. Sci. USA 79, 7415.

Moss, B. 1996: Genetically engineered poxviruses for recombinant gene expression, vaccination, and safety. Proc. Natl. Acad. Sci. USA 93,11341.

Sambrook, et al., 1989, Molecular Cloning: a laboratory manual, Cold Spring Harbor Laboratory Press publication, New York.

Shida, H. et al., 1987, Effect of the recombinant vaccinia viruses that express 30 HTLV-I envelope gene on HTLV-I infection. EMBO J. November;6(11):3379–84.

Sutter, G. et al. 1994 a: A recombinant vector derived from the host range-restricted and highly attenuated MVA strain of vaccinia virus stimulates protective immunity in mice to influenza virus. Vaccine 12, 1032.

Sutter, G. et al. 1994b: Stable expression of the vaccinia virus K1L gene in rabbit cells complements the host range defect of a vaccinia virus mutant. J. Virol. 68, 4109.

What is claimed is:

1. An isolated nucleic acid sequence from the ATI region of modified vaccinia Ankara virus that hybridizes under stringent conditions to the nucleic acid sequence of SEQ ID NO:1 or its complementary strand which includes multiple cloning sites inserted into an open reading frame or the ECORI site of the isolated nucleic acid sequence, said nucleic acid sequence capable of integration of a heterologous sequence through homologous recombination into an open reading frame or an ECORI site of the ATI region of an orthopoxvirus without interfering with its viral propagation or replication efficiency.

2. The nucleic acid sequence defined in claim 1 that includes as the insertion site for the multiple cloning sites an ECORI site corresponding to position 1063 of SEQ ID NO:1 that hybridizes under stringent conditions to the nucleic acid sequence of SEQ ID NO:1 or its complementary strand.

3. An isolated fragment of a nucleic acid sequence from the ATI region of modified vaccinia Ankara virus consisting essentially of at least 200 base pairs of the nucleic acid sequence that is SEQ ID NO:1, which includes multiple cloning sites inserted into an open reading frame or the ECORI site of the isolated fragment of a nucleic acid sequence, said isolated fragment of a nucleic acid sequence capable of integration of a heterologous sequence through homologous recombination into an open reading frame or an ECORI site of the ATI region of an orthopoxvirus without interfering with its viral propagation or replication efficiency.

4. The isolated fragment of a nucleic acid sequence defined in claim 3 that includes as the insertion site for the multiple cloning sites an ECORI site corresponding to position 1063 of SEQ ID NO:1.

5. A vector for integration of a heterologous sequence into an open reading frame of or into the ECORI site of the ATI region of an orthopoxviral genome having an ATI region, said vector including an isolated nucleic acid sequence from the ATI region of modified vaccinia Ankara virus, that hybridizes under stringent conditions to the nucleic acid sequence of SEQ ID NO:1 or its complementary strand, which includes multiple cloning sites inserted into an open reading frame or the ECORI site of the isolated nucleic acid sequence, said nucleic acid sequence capable of integration of the heterologous sequence through homologous recombination into an open reading frame or the ECORI site of the ATI region of an orthopoxvirus without interfering with its viral propagation or replication efficiency.

6. The vector defined in claim 5 wherein additionally at least one transcriptional control element is included in the insertion site.

7. The vector defined in claim 5 wherein the insertion site is the restriction site ECOR1.

8. The vector defined in claim 6 wherein the at least one transcriptional control element is obtained from a poxvirus genome or is a consensus sequence from a poxvirus genome.

9. The vector defined in claim 5 further comprising at least one heterologous sequence inserted into an open reading frame or the ECORI site of the isolated nucleic acid sequence, said heterologous nucleic acid sequence functionally associated with a transcriptional control element thereof.

10. The vector defined in claim 9 wherein the heterologous nucleic sequence is selected from the group consisting of marker genes, therapeutic genes, host range genes and genes encoding immunogenic epitopes.

11. The vector defined in claim 9 comprising a recombinogenic sequence, which flanks one or more heterologous sequences encoding marker genes, host range genes, and/or a transcriptional element thereof.

12. A vector for integration of a heterologous sequence into an open reading frame of or into the ECORI site of the ATI region of an orthopoxviral genome having an ATI region, said vector including an isolated fragment of a nucleic acid sequence from the ATI region of modified vaccinia Ankara virus consisting essentially of at least 200 base pairs of the nucleic acid sequence that is SEQ ID NO:1, which includes multiple cloning sites inserted into an open reading frame or the ECORI site of the isolated fragment of a nucleic acid sequence, said isolated fragment of the nucleic acid sequence capable of integration of the heterologous sequence through homologous recombination into an open reading frame or an ECORI site of the ATI region of an orthopoxvirus without interfering with its viral propagation or replication efficiency.

13. The vector defined in claim 12 wherein additionally at least one transcriptional control element is included in the insertion site.

14. The vector defined in claim 12 wherein the insertion site is the restriction site ECOR1.

15. The vector defined in claim 13 wherein the at least one transcriptional control element is obtained from a poxvirus genome or is a consensus sequence from a poxvirus genome.

16. The vector defined in claim 12 further comprising at least one heterologous sequence inserted into an open reading frame or the ECORI site of the isolated nucleic acid sequence, said heterologous nucleic acid sequence functionally associated with a transcriptional control element thereof.

17. The vector defined in claim 16 wherein the heterologous sequence is selected from the group consisting of marker genes, therapeutic genes, host range genes and genes encoding immunogenic epitopes.

18. The vector defined in claim 16 comprising a recombinogenic nucleic acid sequence, which flanks one or more heterologous sequences encoding marker genes, host range genes, and/or a transcriptional element thereof.

19. A recombinant orthopoxvirus having an ATI region, comprising in an open reading frame of or in the ECORI site of its ATI region an integrated heterologous nucleic acid sequence wherein said integrated heterologous nucleic acid sequence does not interfere with viral propagation and/or replication efficiency.

20. The recombinant orthopoxvirus defined in claim 19 wherein the orthopoxvirus is selected from the group consisting of a modified vaccinia Ankara virus, vaccinia virus Western Reserve, and vaccinia virus Copenhagen.

21. The recombinant orthopoxvirus defined in claim 19 wherein the orthopoxvirus is the modified vaccinia Ankara virus.

22. The recombinant orthopoxvirus defined in claim 19 wherein the heterologous sequence integrated into the orthopoxvirus in its ATI region is from the ATI region of modified vaccinia Ankara virus.

23. The recombinant orthopoxvirus defined in claim 22 wherein the orthopoxvirus is selected from the group consisting of a modified vaccinia Ankara virus, vaccinia virus Western Reserve, and vaccinia virus Copenhagen.

24. The recombinant orthopoxvirus defined in claim 22 wherein the orthopoxvirus is the modified vaccinia Ankara virus.

25. A recombinant orthopoxvirus comprising an ATI region including within an open reading frame of or within the ECORI site of the ATI region an integrated heterologous sequence wherein said recombinant orthopoxvirus is obtained by a method comprising the steps of:
    (a) transducing a host cell with a vector which comprises an isolated nucleic acid sequence from the ATI region of modified vaccinia Ankara virus, that hybridizes under stringent conditions to the nucleic acid sequence of SEQ ID NO:1 or its complementary strand, said nucleic acid sequence capable of integration of the heterologous sequence through homologous recombination into an open reading frame or the ECORI site of the ATI region of an orthopoxvirus without interfering with its viral propagation or replication efficiency, and at least one heterologous sequence inserted into an open reading frame or the ECORI site of the isolated nucleic acid sequence;
    (b) infecting said host cell with an orthopoxvirus having an ATI region;
    (c) integrating the heterologous sequence into an open reading frame or the ECORI site of the ATI region of the orthopoxvirus by homologous recombination between the nucleic acid sequence and a corresponding genomic sequence of the orthopoxvirus to obtain a recombinant orthopoxvirus; and
    (d) isolating said recombinant orthopoxvirus.

26. A recombinant orthopoxvirus comprising an ATI region including within an open reading frame of or within the ECORI site of the ATI region an integrated heterologous sequence wherein said recombinant orthopoxvirus is obtained by a method comprising the steps of:
    (a) transducing a host cell with a vector which comprises an isolated fragment of a nucleic acid sequence from the ATI region of modified vaccinia Ankara virus consisting essentially of at least 200 base pairs of the nucleic acid sequence that is SEQ ID NO:1, said isolated fragment of the nucleic acid sequence capable of integration of the heterologous sequence through homologous recombination into an open reading frame or an ECORI site of the ATI region of an orthopoxvirus without interfering with its viral propagation or replication efficiency and at least one heterologous sequence inserted into an open reading frame or the ECORI site of the isolated nucleic acid sequence;
    (b) infecting said host cell with an orthopoxvirus having an ATI region;
    (c) integrating the heterologous sequence into an open reading frame or the ECORI site of the ATI region of the orthopoxvirus by homologous recombination between the isolated fragment of the nucleic acid sequence and a corresponding genomic sequence of the orthopoxvirus to obtain a recombinant orthopoxvirus; and
    (d) isolating said recombinant orthopoxvirus.

27. A recombinant orthopoxvirus comprising an ATI region including within an open reading frame of or within the ECORI site of the ATI region an integrated heterologous sequence wherein said recombinant orthopoxvirus is obtained by a method comprising the steps of:
    (a) transducing a host cell with a vector which comprises an isolated nucleic acid sequence according to SEQ ID NO:1 or its complementary strand from the ATI region of modified vaccinia Ankara virus, and that is capable of integration of the heterologous sequence into an open reading frame or an ECORI site of the ATI region of an orthopoxvirus without interfering with its viral propagation or replication efficiency, and at least one heterologous sequence inserted site into an open reading frame or the ECORI site of the isolated nucleic acid sequence;
    (b) infecting said host cell with an orthopoxvirus having an ATI region;
    (c) integrating the heterologous sequence into an open reading frame or the ECORI site of the ATI region of the orthopoxvirus by homologous recombination between the nucleic acid sequence and a corresponding genomic sequence of the orthopoxvirus to obtain a recombinant orthopoxvirus; and
    (d) isolating said recombinant orthopoxvirus.

28. A method of integrating a heterologous sequence into an open reading frame or the ECORI site of the ATI region of an orthopoxvirus to obtain a recombinant orthopoxvirus which comprises-the steps of:
    (a) transducing a host cell with a vector comprising an isolated nucleic acid sequence from the ATI region of modified vaccinia Ankara virus that hybridizes under stringent conditions to the nucleic acid sequence of SEQ ID NO:1 or its complementary strand, said nucleic acid sequence capable of integration of the heterologous sequence through homologous recombination into an open reading frame or the ECORI site of the ATI region of an orthopoxvirus without interfering with its viral propagation and replication efficiency, and at least one heterologous sequence inserted site into an open reading frame or the ECORI site of the isolated nucleic acid sequence;
    (b) infecting said host cell with an orthopoxvirus having an ATI region;

(c) integrating the heterologous sequence into an open reading frame or the ECORI site of the ATI region of the orthopoxvirus by homologous recombination between the nucleic acid sequence and a corresponding genomic sequence of the orthopoxvirus to obtain a recombinant orthopoxvirus; and (d) isolating said recombinant orthopoxvirus.

29. The method of integrating a heterologous sequence into the open reading frame or the ECORI site of the ATI region of the orthopoxvirus defined in claim 28 wherein according to step (b) the orthopoxvirus is modified vaccinia Ankara virus.

30. A method of integrating a heterologous sequence into an open reading frame or the ECORI site of the ATI region of an orthopoxvirus to obtain a recombinant orthopoxvirus which comprises the steps of:

(a) transducing a host cell with a vector comprising an isolated fragment of a nucleic acid sequence from the ATI region of modified vaccinia Ankara virus consisting essentially of at least 200 base pairs of the nucleic acid sequence that is SEQ ID NO:1, said isolated fragment of the nucleic acid sequence capable of integration of the heterologous sequence into the ATI region of an orthopoxvirus through homologous recombination into an open reading frame or an ECORI site of the ATI region without interfering with its viral propagation or replication efficiency and at least one heterologous sequence inserted within the insertion site;

(b) infecting said host cell with an orthopoxvirus having an ATI region;

(c) integrating the heterologous sequence into an open reading frame or the ECORI site of the ATI region of the orthopoxvirus by homologous recombination between the isolated fragment of the nucleic acid sequence and a corresponding genomic sequence of the orthopoxvirus to obtain a recombinant orthopoxvirus; and (d) isolating said recombinant orthopoxvirus.

31. The method of integrating a heterologous sequence into an open reading frame or the ECORI site of the ATI region of the orthopoxvirus defined in claim 30 wherein according to step (b) the orthopoxvirus is modified vaccinia Ankara virus.

32. A target cell comprising the recombinant orthopoxvirus defined in claim 19.

33. A pharmaceutical composition for effecting an immune response against an infectious disease or a proliferative disorder which consists essentially of a therapeutically effective amount of the recombinant orthopoxvirus as defined in claim 19 and in a form capable of producing an immune response against an infectious disease or a proliferative disorder in combination with a pharmaceutically acceptable inert carrier or diluent.

34. A method of effecting an immune response against an infectious disease or a proliferative disorder in an animal subject which comprises the step of administering to said subject a therapeutically effective amount of the pharmaceutical composition defined in claim 33.

35. A vector for integration of a heterologous sequence into an open reading frame of or into the ECORI site of the ATI region of an orthopoxviral genome having an ATI region, said vector including an isolated nucleic acid sequence from the ATI region of modified vaccinia Ankara virus, that hybridizes under stringent conditions to the nucleic acid sequence of SEQ ID NO:1 or its complementary strand, which includes at least one heterologous sequence inserted into an open reading frame or the ECORI site of the isolated nucleic acid sequence, said at least one heterologous sequence functionally associated with a transcriptional control element thereof, said isolated nucleic acid sequence capable of integration of the heterologous sequence through homologous recombination into an open reading frame or the ECORI site of the ATI region of an orthopoxvirus without interfering with its viral propagation or replication efficiency.

36. A vector for integration of a heterologous sequence into an open reading frame of or into the ECORI site of the ATI region of an orthopoxviral genome having an ATI region, said vector including an isolated fragment of a nucleic acid sequence from the ATI region of modified vaccinia Ankara virus consisting essentially of at least 200 base pairs of the nucleic acid sequence that is SEQ ID NO:1, which includes at least one heterologous sequence inserted into an open reading frame or the ECORI site of the isolated fragment of a nucleic acid sequence, and which is functionally associated with a transcriptional control element thereof, said isolated fragment of the nucleic acid sequence capable of integration of the heterologous sequence through homologous recombination into an open reading frame or an ECORI site of the ATI region of an orthopoxvirus without interfering with its viral propagation or replication efficiency.

* * * * *

SEQUENCE LISTING

<160> NUMBER OF SEQ ID NOS: 3

<210> SEQ ID NO 1
<211> LENGTH: 1736
<212> TYPE: DNA
<213> ORGANISM: Modified vaccinia Ankara virus
<220> FEATURE:

<400> SEQUENCE: 1

```
ctcgagtaag agcggctatg atatctctgg ctaaaaagat tgatgttcag actggacggc     60
gtccatatga gtaacttaac tcttttgtta attaaaagta tattcaaaaa atgagttata    120
taaatggcga acattataaa tttatggaac ggaattgtac caacggttca agatgttaat    180
gttgcgagca ttactgcgtt taaatctatg atagatgaaa catgggataa aaaaatcgaa    240
gcaaatacat gcatcagtag aaaacataga aacattattc acgaagttat tagggacttt    300
atgaaagcat atcctaaaat ggacgagaat agaaaatctc cattaggagc tccaatgcaa    360
tggctaacac aatattatat tttaaagaat gaatatcata agaccatgct agcgtatgat    420
aatggatcat tgaatacaaa atttaaaacg ttaaacattt atatgattac taacgttggt    480
caatatattt tatatatagt attttgtata atatctggta agaatcacga tggtactcct    540
tatatatacg attctgagat aacgagcaat gataaaaatc ttattaatga gcgtatcaag    600
tatgcatgta agcaaatatt acacggtcaa ttaactatag ctctgagaat tagaaataaa    660
ttcatgttta taggatcacc catgtattta tggtttaacg taaacggatc acaggtatat    720
cacgacatat atgatcgtaa tgccggtttt cataataaag agataggtag actactatac    780
gcatttatgt actatctatc tatctataag tggtagattt ttgaatgatt tcgcactatt    840
aaagtttacg tatttaggag aatcctggac atttagtttg agtgttcctg aatatatatt    900
atatggttta ggatattctg ttttcgatac tattgaaaaa tttagcaatg atgctatact    960
cgtttatgtt agaacaaaca atagaaatgg atatgattat gttgagttta ataaaaaagg   1020
aattgctaag gtgacagaag cctaaacccg ataacgataa gcgaattcat gctataagac   1080
gcatgaaggc tgaacgtgaa atcgctcgta aaaactgcgg aggtaaccca tgcgaacgtg   1140
aattgaaatc tgaacgtagt aacgtgaaga ggttggaata tcaactagat gctgagaaag   1200
aaaaagttaa gttctacaaa agagaactag aacgtgatcg gtatctttct agtagatatc   1260
ttacctcttc ttcagatcca catgagaaac cattaccaaa ttatacattt cctcgcatta   1320
aaaatgtatc tccgttgaca actgaggcta caggttctgt agaagtagca cctccatcca   1380
cagacgttac cgaaccgatt agtgatgtga caccatcggt ggatgtcgaa ccagaacatc   1440
ccccagcttt ctgaatatca gacttcagta tcccaagtag cagttacacc tccaccaaaa   1500
cctgaaactc cacagatttt cgaatatcag acgtccgatt ctatagttaa caatccacgc   1560
ccattttata attcggatct cgaatttgat gatattgata tgtatctact accaaactag   1620
aatattacac cagaaaagac ggcttgagat caactttatc taatggttta taaaacgaag   1680
gaggccttcg ttcgaaatct aatttgactt ttacgcctct ggcgttcatt aagctt       1736
```

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:
oligonucleotide primer

```
<400> SEQUENCE: 2
ccgaagctta atgaacgcca gagg                                              24

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 3
aggctcgagt aagagcggct atgat                                             25
```